(12) United States Patent
Clayton et al.

(10) Patent No.: US 10,149,794 B2
(45) Date of Patent: Dec. 11, 2018

(54) SURGICAL TABLE AND METHOD OF OPERATING THE SAME

(71) Applicant: Eschmann Holdings Limited, Lancing, West Sussex (GB)

(72) Inventors: Matt Clayton, Lancing (GB); Mick Gray, Lancing (GB)

(73) Assignee: Eschmann Holdings Limited (GB)

( * ) Notice: Subject to any disclaimer, the term of this patent is extended or adjusted under 35 U.S.C. 154(b) by 32 days.

(21) Appl. No.: 14/896,938

(22) PCT Filed: Jun. 14, 2014

(86) PCT No.: PCT/EP2014/062471
§ 371 (c)(1),
(2) Date: Dec. 9, 2015

(87) PCT Pub. No.: WO2014/198949
PCT Pub. Date: Dec. 18, 2014

(65) Prior Publication Data
US 2016/0106611 A1    Apr. 21, 2016

(30) Foreign Application Priority Data
Jun. 14, 2013  (GB) .................................. 1310671.1

(51) Int. Cl.
*A47B 7/02* (2006.01)
*A61G 13/08* (2006.01)
(Continued)

(52) U.S. Cl.
CPC ............. *A61G 13/08* (2013.01); *A61G 13/02* (2013.01); *A61G 13/06* (2013.01); *A47C 19/04* (2013.01);
(Continued)

(58) Field of Classification Search
CPC ........ A61G 13/08; A61G 13/02; A61G 13/06; A61G 13/04; A61G 13/0036;
(Continued)

(56) References Cited

U.S. PATENT DOCUMENTS

| 4,159,822 A * | 7/1979 | Ota | ........................ A47C 3/30 5/614 |
| 4,769,584 A * | 9/1988 | Irigoyen | ................ A61G 7/018 318/281 |

(Continued)

FOREIGN PATENT DOCUMENTS

| CN | 2211745 | 11/1995 |
| EP | 0630637 A1 | 12/1994 |

(Continued)

OTHER PUBLICATIONS

Int'l. Search Report and Written Opinion dated Oct. 28, 2014 in priority application PCT/EP2014/064472.

(Continued)

*Primary Examiner* — Nicholas F Polito
*Assistant Examiner* — Morgan J McClure
(74) *Attorney, Agent, or Firm* — Polsinelli PC

(57) ABSTRACT

A surgical table includes a mechanism for causing movement of a tabletop of the table relative to a column of the table in a selected longitudinal or transverse direction of the tabletop, the mechanism including first and second drive elements movably mounted on one of the column and the tabletop and a traverse device mounted on the other of the column and the tabletop, wherein the tabletop is movable relative to the column between a predetermined traverse position, at which both of the first and second drive elements are engaged with the traverse device, and a first traverse position, at which the first drive element is engaged with the traverse device and the second drive element is disengaged (Continued)

from the traverse device. Also described is a system for helping a user dispose a tabletop of a table a predetermined position relative to a column of the table.

18 Claims, 4 Drawing Sheets

(51) Int. Cl.

| | | |
|---|---|---|
| *A61G 13/02* | (2006.01) | |
| *A61G 13/06* | (2006.01) | |
| *A47C 19/04* | (2006.01) | |
| *A61B 6/04* | (2006.01) | |
| *A61G 5/10* | (2006.01) | |
| *A61G 13/04* | (2006.01) | |

(52) U.S. Cl.
CPC ............ *A61B 6/0407* (2013.01); *A61G 5/107* (2013.01); *A61G 13/04* (2013.01); *A61G 2203/10* (2013.01); *A61G 2203/40* (2013.01)

(58) Field of Classification Search
CPC .............. A61G 13/0054; A61G 13/122; A61G 13/123; A61G 13/104; A61G 13/121; A61G 2203/10; A61G 2203/40; A61G 2210/50; A61G 5/107; A61B 6/0407; A47C 19/045; A47C 19/04
See application file for complete search history.

(56) References Cited

U.S. PATENT DOCUMENTS

| | | | | |
|---|---|---|---|---|
| 5,210,893 | A * | 5/1993 | Uosaki ................ | A61B 5/0555 5/600 |
| 5,381,572 | A * | 1/1995 | Park ........................ | A47D 9/02 5/109 |
| 5,398,356 | A * | 3/1995 | Pfleger ..................... | A61B 6/04 5/601 |
| 5,490,297 | A * | 2/1996 | Bradcovich .......... | A61B 5/0555 108/147 |
| 5,586,346 | A * | 12/1996 | Stacy ................ | A61G 7/05769 5/706 |
| 5,628,078 | A * | 5/1997 | Pennington .............. | A61B 6/06 5/613 |
| 5,659,909 | A * | 8/1997 | Pfeuffer ................. | A61G 13/08 5/600 |
| 5,778,467 | A * | 7/1998 | Scott ................... | A61G 13/009 5/612 |
| 6,240,582 | B1* | 6/2001 | Reinke ................ | A61B 6/0457 378/209 |
| 6,578,215 | B1* | 6/2003 | Heimbrock ............ | A61G 13/08 5/617 |
| 6,615,428 | B1* | 9/2003 | Pattee ..................... | A61B 6/04 108/143 |
| 6,955,464 | B1* | 10/2005 | Tybinkowski ....... | A61B 6/0457 108/143 |
| 7,089,612 | B2* | 8/2006 | Rocher ................. | A61G 13/08 5/600 |
| 7,103,931 | B2* | 9/2006 | Somasundaram ... | A61B 6/0457 378/209 |
| 7,131,769 | B2* | 11/2006 | Vezina ..................... | A61B 6/04 378/209 |
| 7,266,406 | B2* | 9/2007 | Kroeckel ......... | G01R 33/34084 324/307 |
| 7,430,772 | B2* | 10/2008 | Van Es ................ | A61B 5/0555 378/209 |
| 7,437,785 | B2* | 10/2008 | Farooqui ............ | A61B 6/0457 378/209 |
| 7,552,490 | B2* | 6/2009 | Saracen ............... | A61B 6/0457 378/209 |
| 7,631,749 | B2* | 12/2009 | Somasundaram ..... | A61G 13/02 198/468.9 |
| 7,634,827 | B2* | 12/2009 | Gagneur ................ | A61B 5/704 378/209 |
| 7,784,127 | B2* | 8/2010 | Kuro ..................... | A61B 6/0457 318/375 |
| 7,810,187 | B2* | 10/2010 | Van Es ................ | A61B 6/0457 378/209 |
| 8,117,694 | B2* | 2/2012 | Farooqui .............. | A61B 6/0457 198/468.9 |
| 8,126,537 | B2* | 2/2012 | Yakubovsky .......... | A61B 6/032 5/601 |
| 8,381,331 | B2* | 2/2013 | Sharps ................... | A61G 7/001 5/607 |
| 8,565,982 | B2* | 10/2013 | Lofstrand ................ | A61G 5/04 280/35 |
| 8,621,689 | B2* | 1/2014 | Dong ..................... | A61B 5/0555 5/600 |
| 8,661,584 | B1* | 3/2014 | Yang .................... | A61B 6/0457 378/209 |
| 8,690,178 | B2* | 4/2014 | Griswold ................. | A61G 5/10 280/250.1 |
| 8,869,327 | B2* | 10/2014 | Eder ..................... | A61B 6/0407 378/209 |
| 8,931,125 | B2* | 1/2015 | Fang ..................... | F16H 37/124 108/137 |
| 9,061,141 | B2* | 6/2015 | Brunker ............... | A61B 6/0442 |
| 9,192,534 | B2* | 11/2015 | Coppens ................ | A61G 7/103 |
| 9,282,937 | B2* | 3/2016 | Shibata ................. | A61B 6/0407 |
| 9,351,584 | B1* | 5/2016 | Rizzardo ............. | A47C 19/045 |
| 9,446,260 | B2* | 9/2016 | Jagger .................. | A61N 5/0613 |
| 9,463,127 | B2* | 10/2016 | Hochman ............ | A61G 7/1057 |
| 9,549,706 | B2* | 1/2017 | Zhang .................. | A61B 6/0407 |
| 9,636,184 | B2* | 5/2017 | Lee ........................ | A61B 34/30 |
| 9,642,757 | B2* | 5/2017 | Sheppard .............. | A61G 7/015 |
| 9,681,848 | B2* | 6/2017 | Goto ...................... | A61B 6/4464 |
| 2002/0029419 | A1* | 3/2002 | Weil ..................... | A61B 6/0457 5/601 |
| 2002/0170116 | A1 | 11/2002 | Borders et al. | |
| 2004/0098804 | A1* | 5/2004 | Varadharajulu ...... | A61B 6/0457 5/611 |
| 2004/0172757 | A1* | 9/2004 | Somasundaram ..... | A61B 6/105 5/601 |
| 2004/0187213 | A1* | 9/2004 | Wang ..................... | A61G 7/012 5/618 |
| 2006/0242765 | A1 | 11/2006 | Skripps et al. | |
| 2007/0136947 | A1 | 6/2007 | Limpert | |
| 2008/0016620 | A1 | 1/2008 | Haras | |
| 2008/0235872 | A1* | 10/2008 | Newkirk ................ | A61G 7/018 5/600 |
| 2010/0235995 | A1 | 9/2010 | Liang | |
| 2011/0277241 | A1 | 11/2011 | Schejbal | |
| 2012/0063838 | A1 | 3/2012 | Sahu et al. | |
| 2012/0205509 | A1 | 8/2012 | Marugg | |
| 2013/0019883 | A1 | 1/2013 | Worm et al. | |
| 2013/0081489 | A1 | 4/2013 | Fang et al. | |
| 2013/0129416 | A1 | 5/2013 | Huggler et al. | |
| 2013/0152307 | A1 | 6/2013 | Bennett-Guerrero | |
| 2013/0312191 | A1* | 11/2013 | Szeinberg ............ | A61G 7/0573 5/632 |
| 2015/0135440 | A1* | 5/2015 | Chiacchira ............. | A61G 7/015 5/611 |
| 2015/0323388 | A1* | 11/2015 | Kostic .................... | A61G 13/10 250/338.1 |

FOREIGN PATENT DOCUMENTS

| | | |
|---|---|---|
| EP | 0917867 A1 | 5/1999 |
| JP | 1297054 | 11/1989 |
| JP | 06114087 | 4/1994 |
| WO | 200000152 A1 | 1/2000 |
| WO | 2002023057 A1 | 3/2002 |
| WO | 2002058617 A2 | 8/2002 |
| WO | 200303802 A2 | 4/2003 |
| WO | 2004105603 A1 | 9/2004 |
| WO | 2010039102 A1 | 8/2010 |
| WO | 2013069952 A1 | 5/2013 |

(56) References Cited

FOREIGN PATENT DOCUMENTS

OTHER PUBLICATIONS

Search and Examination Report dated Dec. 4, 2013 in priority application GB1312307.0.
Search and Examination Report dated May 12, 2016 in corresponding application GB1606232.5.
Int'l. Search Report and Written Opinion dated Mar. 20, 2015 from priority application PCT/EP2014/064473.
Search and Examination Report dated Dec. 4, 2013 from priority application GB1312522.4.
Search and Examination Report dated May 27, 2016 in corresponding application GB 1606240.8.
Int'l. Search Report and Written Opinion dated Jan. 7, 2015 in corresponding application PCT/EP2014/062471.
Combined Search and Examination Report under Sections 17 and 18(3) dated Dec. 5, 2013 in corresponding application GB1310671.1.
Combined Search and Examination Report under Sections 17 and 18(3) dated Jun. 1, 2015 in corresponding application GB1508042.7.
Int'l. Preliminary Report on Patentability dated Dec. 15, 2015 in corresponding Int'l. Application No. PCT/EP2014/062471.
Int'l. Search Report and Written Opinion dated Jan. 7, 2015 in Int'l. Appln. No. PCT/EP2014/062471.

\* cited by examiner

SURGICAL TABLE AND METHOD OF OPERATING THE SAME

FIELD OF THE INVENTION

The present invention relates to surgical tables and to methods of operating surgical tables.

BACKGROUND

Surgical tables, or operating tables, comprising a base for standing on a floor, a column extending from the base, and a tabletop providing a patient support surface are well known.

In order for surgical tables to be versatile, it is necessary for the tabletop to be disposable in a variety of different configurations. WO2003/030802 discloses a surgical table with mechanisms for inclining a tabletop of the table relative to a column of the table and relative to the horizontal about both transverse and longitudinal axes of the tabletop, and a drive assembly for permitting a traverse movement of the tabletop relative to the column in back and forth longitudinal directions of the tabletop.

Anthropometric data of the world's population is shifting over time.

SUMMARY OF THE INVENTION

There is a need for a surgical table with a more compact mechanism for disposing a tabletop in a variety of different configurations.

There also is a need for a surgical table with a mechanism for disposing a tabletop in a greater variety of different configurations, in order to increase the versatility of the surgical table for serving the population as anthropometric data shifts over time.

Surgical tables may have a tabletop and a column that are movable relative to each other between first and second relative positions via a predetermined relative position, such as a predetermined default or home position. Such a predetermined relative position may be, for example, the position at which a patient is most easily transferrable onto or from the table, the position at which the table is most stable, or the position at which the table is best placed to enable a certain procedure to be performed on a patient supported by the table.

There is a need for a surgical table having an assistance mechanism for helping medical staff using the surgical table to dispose a tabletop and a column of a surgical table at such a predetermined relative position.

A first aspect of the present invention provides a surgical table comprising: a base for standing on a floor; a column extending from the base; a tabletop providing a patient support surface; and a tabletop traverse drive mechanism coupling the tabletop to the column, which tabletop traverse drive mechanism is for causing movement of the tabletop relative to the column in a selected longitudinal or transverse direction of the tabletop; wherein the tabletop traverse drive mechanism comprises a driver, first and second drive elements that are drivable by the driver, and a traverse device that is drivable by each of the first and second drive elements, the first and second drive elements being movably mounted on one of the column and the tabletop and the traverse device being mounted on the other of the column and the tabletop; and wherein the driver is operable to drive the first and second drive elements to drive the traverse device to cause movement of the tabletop relative to the column between a predetermined traverse position, at which both of the first and second drive elements are engaged with the traverse device, and a first traverse position, at which the first drive element is engaged with the traverse device and the second drive element is disengaged from the traverse device.

Optionally, the driver is operable to drive the first and second drive elements to drive the traverse device to cause movement of the tabletop relative to the column to a second traverse position, at which the second drive element is engaged with the traverse device and the first drive element is disengaged from the traverse device.

Optionally, the first and second drive elements are movably mounted on the column and the traverse device is mounted on the tabletop.

Optionally, the first and second drive elements are rotatably mounted on the one of the column and the tabletop.

Optionally, the first and second drive elements are mounted for rotation about respective first and second axes that are both perpendicular to the longitudinal direction of the tabletop, or that are both parallel to the longitudinal direction of the tabletop. Optionally, one or each of the first and second axes is perpendicular to a lateral direction of the tabletop, which lateral direction of the tabletop is perpendicular to the longitudinal direction of the tabletop. Optionally, one or each of the first and second axes is parallel to a lateral direction of the tabletop, which lateral direction of the tabletop is perpendicular to the longitudinal direction of the tabletop.

Optionally, the first and second drive elements are meshed with the traverse device when the tabletop is at the predetermined traverse position.

Optionally, the first and second drive elements are first and second pinion gears.

Optionally, the traverse device is a rack.

Optionally, the traverse device is linear and aligned with the longitudinal direction of the tabletop.

Optionally, the first and second drive elements are spaced apart in a direction that is parallel to the longitudinal direction of the tabletop.

Optionally, the driver comprises a motor connected to both the first and second drive elements for driving both the first and second drive elements.

Optionally, the surgical table comprises a controller for controlling operation of the tabletop traverse drive mechanism. Optionally, the controller is configured to control the tabletop traverse drive mechanism to cause movement of the tabletop relative to the column between the first and second traverse positions via the predetermined traverse position, and configured, when the tabletop is at the predetermined traverse position relative to the column, to control the tabletop traverse drive mechanism to cause the movement of the tabletop relative to the column to be paused for a predetermined period of time.

Optionally, the surgical table comprises a sensor for sensing, and for notifying the controller of, a relative position of the tabletop and the column. Optionally, the sensor is for sensing, and for notifying the controller of, when the tabletop is at the predetermined traverse position relative to the column.

Optionally, the predetermined period of time is between 0.05 and 5 seconds. Further optionally, the predetermined period of time is between 0.1 and 3 seconds. Further optionally, the predetermined period of time is between 0.25 and 2 seconds.

A second aspect of the present invention provides a surgical table comprising a base for standing on a floor; a column extending from the base; a tabletop providing a patient support surface; a tabletop traverse drive mechanism coupling the tabletop to the column, which tabletop traverse drive mechanism is for causing movement of the tabletop relative to the column in a selected longitudinal or transverse direction of the tabletop; and a controller for controlling operation of the tabletop traverse drive mechanism; wherein the controller is configured to control the tabletop traverse drive mechanism to cause movement of the tabletop relative to the column between first and second traverse positions via a predetermined traverse position, and configured, when the tabletop is at the predetermined traverse position relative to the column, to control the tabletop traverse drive mechanism to cause the movement of the tabletop relative to the column to be paused for a predetermined period of time.

Optionally, the tabletop traverse drive mechanism is for causing movement of the tabletop relative to the column in a selected longitudinal direction of the tabletop.

Optionally, the surgical table comprises a sensor for sensing, and for notifying the controller of, a relative position of the tabletop and the column. Optionally, the sensor is for sensing, and for notifying the controller of, when the tabletop is at the predetermined traverse position relative to the column.

Optionally, the predetermined period of time is between 0.05 and 5 seconds. Further optionally, the predetermined period of time is between 0.1 and 3 seconds. Further optionally, the predetermined period of time is between 0.25 and 2 seconds.

A third aspect of the present invention provides a method of operating a surgical table having a base for standing on a floor; a column extending from the base; a tabletop providing a patient support surface; a tabletop traverse drive mechanism coupling the tabletop to the column, which tabletop traverse drive mechanism is for causing movement of the tabletop relative to the column in a selected longitudinal or transverse direction of the tabletop; and a controller for controlling operation of the tabletop traverse drive mechanism, the method comprising: the controller controlling the tabletop traverse drive mechanism to cause movement of the tabletop relative to the column between first and second traverse positions via a predetermined traverse position; and the controller controlling the tabletop traverse drive mechanism to cause the movement of the tabletop relative to the column to be paused for a predetermined period of time when the tabletop is at the predetermined traverse position relative to the column.

Optionally, the tabletop traverse drive mechanism is for causing relative movement of the tabletop relative to the column in a selected longitudinal direction of the tabletop.

Optionally, the method comprises sensing a relative position of the tabletop and the column. Further optionally, the method comprises sensing when the tabletop is at the predetermined traverse position relative to the column.

Optionally, the predetermined period of time is between 0.05 and 5 seconds. Further optionally, the predetermined period of time is between 0.1 and 3 seconds. Further optionally, the predetermined period of time is between 0.25 and 2 seconds.

A fourth aspect of the present invention provides a computer program product for causing a surgical table to perform the method of the third aspect of the present invention.

BRIEF DESCRIPTION OF THE FIGURES

Preferred embodiments of the present invention will now be described by way of example only with reference to the accompanying drawings, in which.

DETAILED DESCRIPTION

Figure 1:
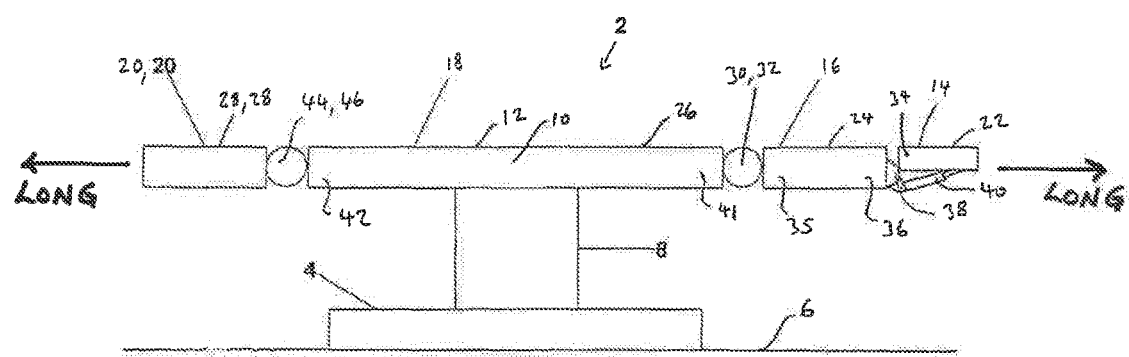
FIG. 1 is a schematic side view of a surgical table in accordance with an embodiment of the present invention.

Referring to FIG. 1, a surgical table, designated generally as 2, includes a base 4, which stands on a floor 6, a column 8 of adjustable height extending from the base 4 and a tabletop 10 providing a patient support surface 12. In a variation to this embodiment, the column 8 is not of adjustable height. The base 4 may include wheels for moving the table 2 along the floor 6.

As depicted in FIG. 1, the tabletop 10 is divided into five sections, namely a head section 14, an upper torso section 16, a lower torso section 18 and a pair of laterally adjacent leg sections 20, 20, of which only one is shown in FIG. 1. Each of the sections of the tabletop 10 provides a portion of the patient support surface 12, and each of the sections has a respective separate mattress 22, 24, 26, 28, 28.

The lower torso section 18 is coupled to the column 8. A lower end 35 of the upper torso section 16 is detachably mounted on an upper end 41 of the lower torso section 18 by means of transversely adjacent first and second pivot joints 30, 32, which define a transverse axis about which the upper torso section 16 can be displaced relative to the lower torso section 18.

Each of the leg sections 20 is detachably mounted on a lower end 42 of the lower torso section 18 by a respective one of transversely adjacent third and fourth pivot joints 44, 46, of which only one is visible in FIG. 1, for displacement relative to the lower torso section 18 about a transverse axis defined by the respective one of third and fourth pivot joints 44, 46.

A lower end 34 of the head section 14 is detachably mounted on an upper end 36 of the upper torso section 16 by means of a fifth pivot joint 38 defining a transverse axis about which the head section 14 can be displaced relative to the upper torso section 16. The angle of inclination of the head section 14 is controlled manually by means of a pair of conventional adjustable struts 40, only one of which is shown in FIG. 1, secured to and extending between the underside of the head section 14 and the upper torso section 16, one on each side of the tabletop 10. The struts 40 may be hydraulic or electric actuators or lockable gas springs.

The provision of the five pivot joints 30, 32, 38, 44, 46 permits the five sections 14, 16, 18, 20, 20 selectively to be inclined relative to adjacent sections 14, 16, 18, 20, 20 thereby to dispose the tabletop 10 in a selected configuration. Moreover, that the head section 14 is detachable from the upper torso section 16, and each of the upper torso section 16 and the leg sections 20, 20 is detachable from the lower torso section 18 means that the table 2 may be made compact for storage.

Although not expressly shown in the Figures, the surgical table 2 of this embodiment also includes a mechanism for inclining the whole tabletop 10 relative to the column 8 and relative to the horizontal about transverse and longitudinal axes of the tabletop 10. Inclination about the transverse axis of the tabletop 10 is referred to in the art as "trending", while inclination about the longitudinal axis of the tabletop 10 is referred to as "tilting". Compound movements also are possible, in which the tabletop 10 is inclined about both the transverse and longitudinal axes of the tabletop 10 at the same time.

As used herein, the longitudinal axis LONG of the tabletop is the major axis of the tabletop and the transverse axis LAT of the tabletop is the orthogonal minor axis of the tabletop. The longitudinal direction of the tabletop is parallel to the major axis and the transverse direction of the tabletop is parallel to the minor axis. That is, the transverse direction of the tabletop is perpendicular to, or orthogonal to, the longitudinal direction of tabletop.

In variations to the illustrated embodiment, the tabletop 10 may be divided into a different number and/or configuration of sections to those shown in the Figures, or may not be divided into multiple sections at all. In such variations, the tabletop 10 may not include any sections that are relatively inclinable to each other by pivoting about a transverse axis defined by a pivot joint. In some such variations, the table 2 still includes a mechanism for inclining the whole tabletop 10 relative to the column 8 and/or relative to the horizontal about transverse LAT and/or longitudinal LONG axes of the tabletop 10. In other variations, no such mechanism is provided, and the whole tabletop 10 is not inclinable relative to the column 8 and relative to the horizontal.

The surgical table 2 further is provided with a tabletop traverse drive mechanism 100 mounted between the underside of the tabletop 10 and the top of the column 8 for causing movement of the tabletop 10 relative to the column 8 in a selected longitudinal direction of the tabletop 10. The tabletop 10 is coupled to the column 8 via the tabletop traverse drive mechanism 100, with the tabletop traverse drive mechanism 100 permitting relative movement of the tabletop 10 and the column 8. Operation of the tabletop traverse drive mechanism 100 is controlled by a controller (not shown) of the surgical table 2. The controller controls the tabletop traverse drive mechanism 100 in dependence on one or more instructions received at the controller from a user interface (not shown) of the operating table.

Figure 2A:
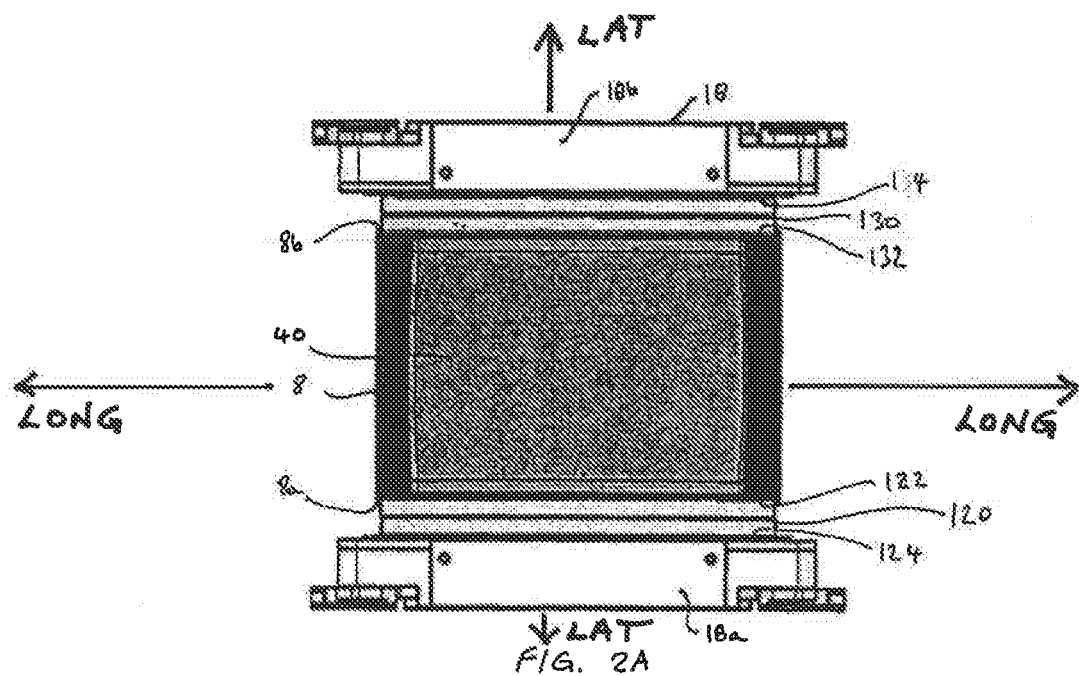
FIG. 2A is a top plan view of a top portion of the column and the lower torso section of the surgical table of FIG. 1, with the mattress of the lower torso section removed and with the lower torso section at a predetermined traverse position relative to the column.
Figure 2B:
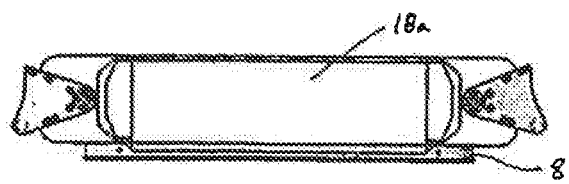
FIG. 2B is a side view of the components shown in FIG. 2A.
Figure 2C:
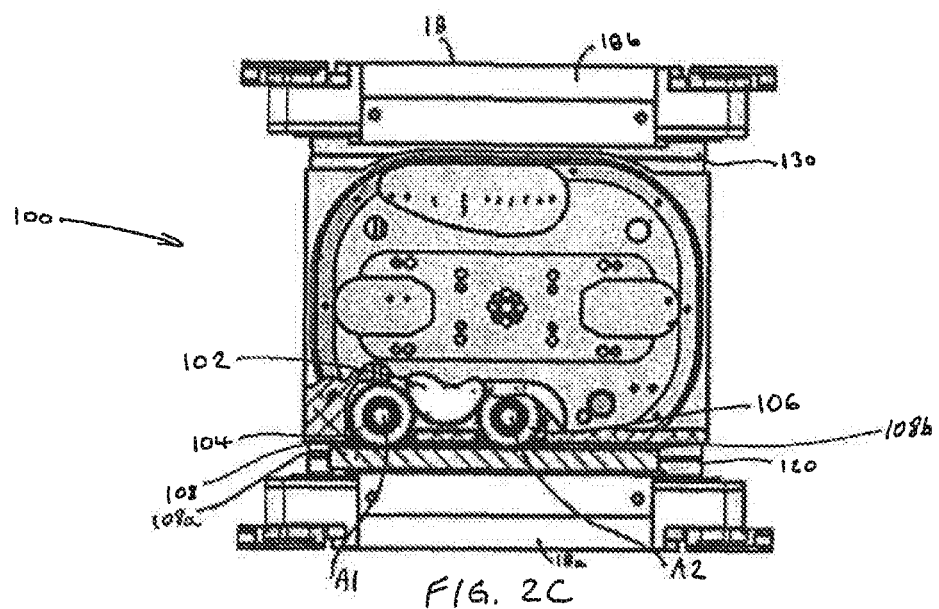
FIG. 2C is a bottom view of the components shown in FIG. 2A.

Referring to FIGS. 2A to 2C, the tabletop traverse drive mechanism 100 comprises a driver in the form of a motor (not shown), a drive gear 102 for being driven by the motor, first and second drive elements in the form of first and second pinion gears 104, 106 that are meshed with the drive gear 102 so as to be drivable by the motor via the drive gear 102, and a traverse device in the form of a rack 108 that is meshed with the first and second pinion gears 104, 106 so as to be drivable by each of the first and second pinion gears 104, 106. The motor may be an electrically-powered motor. Any suitable mechanism for causing the drive gear 102 to be driven by the motor may be provided. For example, the drive gear 102 may be fixed to a spindle of the motor, so that rotation of the spindle about an axis causes rotation of the drive gear 102 about the same axis. Alternatively, the drive gear 102 may be indirectly connected to a spindle of the motor, such as by one or more further gears. For example, a primary gear (not shown), such as a worm gear, may be fixed to the spindle of the motor, which primary gear is meshed with the drive gear 102 so that rotation of the spindle causes rotation of the primary gear which, in turn, causes rotation of the drive gear 102.

In the illustrated embodiment, the motor is mounted on the column 8 beneath a cover 40 covering a top of the column 8, the drive gear 102 and first and second pinion gears 104, 106 are rotatably mounted on the column 8 beneath the cover 40, and the rack 108 is mounted on an inner side of a first frame member 18a of a pair of lateral frame members 18a, 18b of the lower torso section 18 of the tabletop 10. In variations to this embodiment, the motor is mounted on the tabletop 10, the drive gear 102 and first and second pinion gears 104, 106 are rotatably mounted on the tabletop 10, and the rack 108 is mounted on the column 8.

The first and second pinion gears 104, 106 are mounted on the column 8 for rotation about respective first and second axes A1, A2, which axes A1, A2 are both perpendicular to the longitudinal direction of the tabletop 10. Moreover, the axes A1, A2 are both perpendicular to a lateral direction of the tabletop 10, which lateral direction of the tabletop 10 is perpendicular to the longitudinal direction of the tabletop 10. This arrangement minimises the vertical height of the first and second pinion gears 104, 106, which permits the patient support surface 12 to be low. The first and second pinion gears 104, 106, and their respective first and second axes A1, A2, are spaced apart in a direction that is parallel to the longitudinal direction of the tabletop 10, and the rack 108 is linear and aligned with the longitudinal direction of the tabletop 10. That is, the rack 108 has finite length and two opposed ends 108a, 108b that are spaced apart in a direction that is parallel to the longitudinal direction of the tabletop 10.

In variations to the illustrated embodiment, one or each of the axes A1, A2 is parallel to the longitudinal direction of the tabletop 10 or parallel to the lateral direction of the tabletop 10. In some embodiments, one of the axes A1, A2 is perpendicular to the lateral direction of the tabletop 10, while the other of the axes A1, A2 is parallel to the lateral direction of the tabletop 10.

The tabletop traverse drive mechanism 100 further comprises first and second telescopic stabiliser arms 120, 130 slidably connected between respective lateral sides of the column 8 and respective ones of the pair of lateral frame members 18a, 18b of the lower torso section 18 of the tabletop 10. More particularly, a first track 122 of the first telescopic stabiliser arm 120 is slidably engaged with a track 8a on a first lateral side of the column 8, and a second track 124 of the first telescopic stabiliser arm 120 is slidably engaged with a track 18c on the first frame member 18a of the lower torso section 18 of the tabletop 10. Similarly, a first track 132 of the second telescopic stabiliser arm 130 is slidably engaged with a track 8b on a second lateral side of the column 8, and a second track 134 of the second telescopic stabiliser arm 130 is slidably engaged with a track 18d on the second frame member 18b of the upper torso section 16 of the tabletop 10.

Although not expressly shown in the Figures, each of a first pair of cooperable stop features is provided on a respective one of the first track 122 of the first telescopic stabiliser arm 120 and the track 8a on the first lateral side of the column 8, to limit the possible range of movement of the first track 122 relative to the track 8a back and forth in the longitudinal direction of the tabletop 10. Each of a second pair of cooperable stop features is provided on a respective one of the second track 124 of the first telescopic stabiliser arm 120 and the track 18c on the first frame member 18a of the lower torso section 18 of the tabletop 10, to limit the possible range of movement of the second track 124 relative to the track 18c back and forth in the longitudinal direction of the tabletop 10. Each of a third pair of cooperable stop features is provided on a respective one of the first track 132 of the second telescopic stabiliser arm 130 and the track 8b on the second lateral side of the column 8, to limit the possible range of movement of the first track 132 relative to the track 8b back and forth in the longitudinal direction of the tabletop 10. Each of a fourth pair of cooperable stop features is provided on a respective one of the second track 134 of the second telescopic stabiliser arm 130 and the track 18d on the second frame member 18b of the lower torso section 18 of the tabletop 10, to limit the possible range of movement of the second track 134 relative to the track 18d back and forth in the longitudinal direction of the tabletop 10. The first to fourth pairs of cooperable stop features together limit the possible range of movement of the tabletop 10 relative to the column 8 back and forth in the longitudinal direction of the tabletop 10.

Operation of the tabletop traverse drive mechanism 100 will now be described.

In FIGS. 2A to 2C, the tabletop 10 is shown at a predetermined traverse position relative to the column 8 with both of the first and second pinion gears 104, 106 meshed with the rack 108. When a user wishes to traverse the tabletop 10 relative to the column 8, they operate the user interface to cause the user interface to send an instruction to the controller, which causes the controller to cause the motor to be energised, to operate in either a forward or reverse rotational mode in dependence on a content of the instruction from the user interface. The energisation of the motor causes the drive gear 102 to be rotated by the motor, thereby causing the first and second pinion gears 104, 106 to be longitudinally driven along the rack 108. Accordingly, the rack 108, which is rigidly attached to the lower torso section 18 of the tabletop 10, is longitudinally driven back or forth relative to the column 8 to which the first and second pinion gears 104, 106, the drive gear 102 and also the motor, are mounted. This traverses the tabletop 10 back and forth relative to the column 8.

Figure 3A:
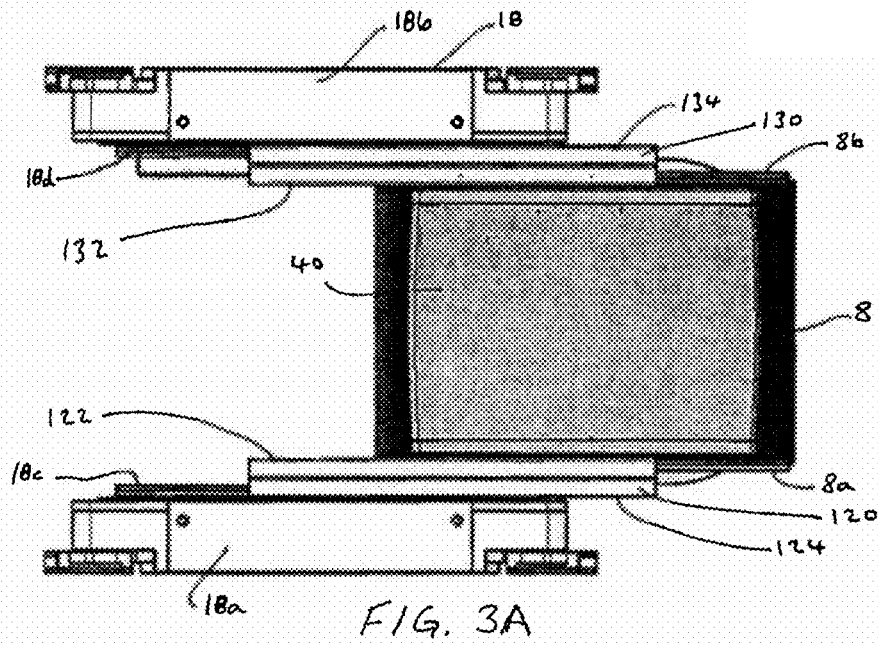
FIG. 3A is a top plan view of a top portion of the column and the lower torso section of the surgical table of FIG. 1, with the mattress of the lower torso section removed and with the lower torso section at a first traverse position relative to the column.
Figure 3B:
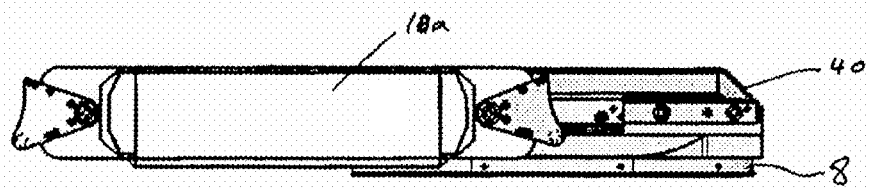
FIG. 3B is a side view of the components shown in FIG. 3A.
Figure 3C:
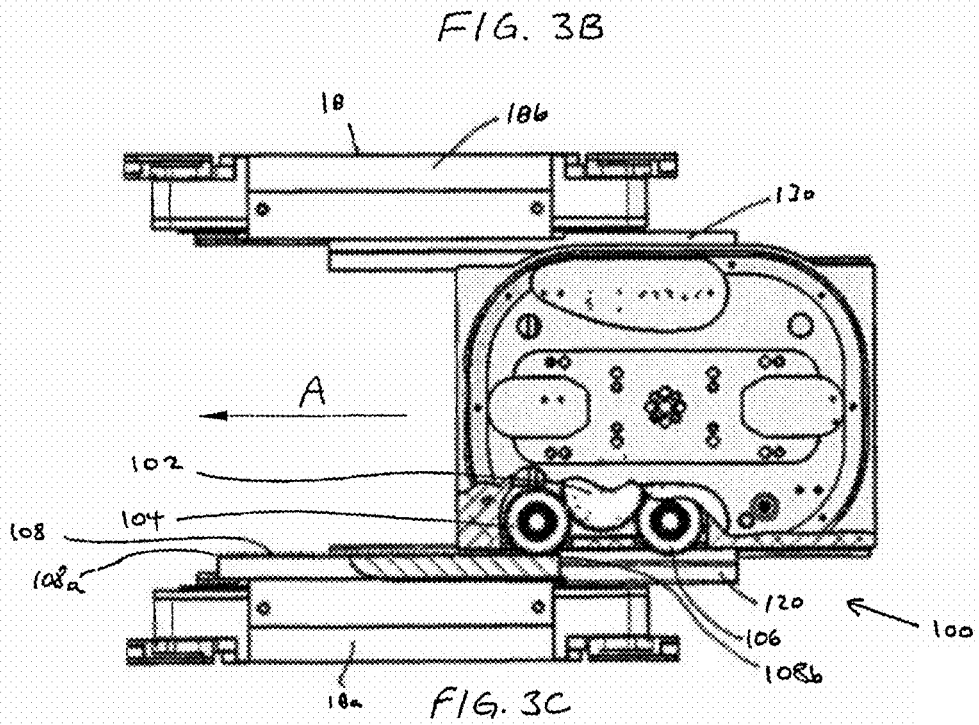
FIG. 3C is a bottom view of the components shown in FIG. 3A.

The controller is operable, via the user interface, to cause the motor to drive the first and second pinion gears 104, 106 to drive the rack 108, in order to cause movement (in the direction of arrow A in FIG. 3C) of the tabletop 10 relative to the column 8 between the predetermined traverse position, illustrated in FIGS. 2A to 2C, and a first traverse position, illustrated in FIGS. 3A to 3C. During movement of the tabletop 10 relative to the column 8 from the predetermined traverse position towards the first traverse position, the first and second pinion gears 104, 106 are driven along the rack 108. Before the tabletop 10 reaches the first traverse position, the second pinion gear 106 is driven off the second end 108b of the rack 108. However, the first pinion gear 104 remains meshed with the rack 108, so that the rack 108 is drivable by the first pinion gear 104 and continued driving of the first pinion gear 104 by the motor continues to move the tabletop 10 relative to the column 8 until the tabletop 10 reaches the first traverse position relative to the column 8. When the tabletop 10 is at the first traverse position relative to the column 8, the first pinion gear 104 still is engaged with the rack 108 but the second pinion gear 106 is disengaged from the rack 108. That is, there is no contact between the second pinion gear 106 and the rack 108.

Figure 4A:
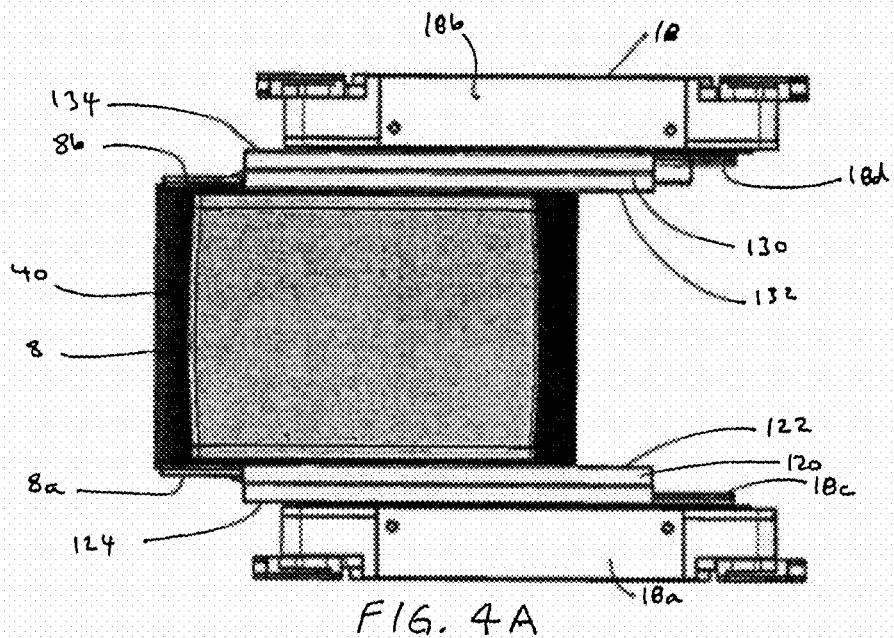
FIG. 4A is a top plan view of a top portion of the column and the lower torso section of the surgical table of FIG. 1, with the mattress of the lower torso section removed and with the lower torso section at a second traverse position relative to the column.
Figure 4B:
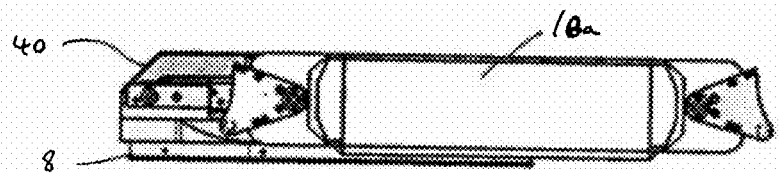
FIG. 4B is a side view of the components shown in FIG. 4A.
Figure 4C:
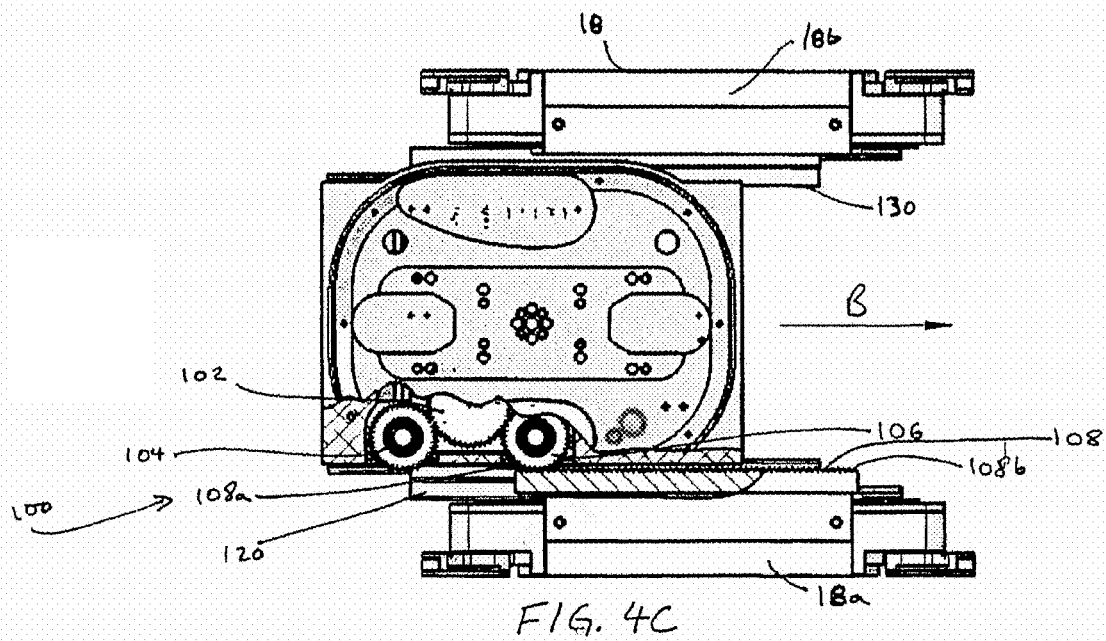
FIG. 4C is a bottom view of the components shown in FIG. 4A.

Similarly, the controller also is operable, via the user interface, to cause the motor to drive the first and second pinion gears 104, 106 to drive the rack 108, in order to cause movement (in the direction of arrow B in FIG. 4C) of the tabletop 10 relative to the column 8 between the predetermined traverse position, illustrated in FIGS. 2A to 2C, and a second traverse position, illustrated in FIGS. 4A to 4C. During movement of the tabletop 10 relative to the column 8 from the predetermined traverse position towards the second traverse position, the first and second pinion gears 104, 106 are driven along the rack 108. Before the tabletop 10 reaches the second traverse position, the first pinion gear 104 is driven off the first end 108a of the rack 108. However, the second pinion gear 106 remains meshed with the rack 108, so that the rack 108 is drivable by the second pinion gear 106 and continued driving of the second pinion gear 106 by the motor continues to move the tabletop 10 relative to the column 8 until the tabletop 10 reaches the second traverse position relative to the column 8. When the tabletop 10 is at the second traverse position relative to the column 8, the second pinion gear 106 still is engaged with the rack 108 but the first pinion gear 104 is disengaged from the rack 108. That is, there is no contact between the first pinion gear 104 and the rack 108.

It will thus be appreciated that, through the provision of the tabletop traverse drive mechanism, the tabletop is movable relative to the column in the longitudinal direction of the tabletop over a distance that is greater than the length of the traverse device (the rack 108, in the illustrated non-limiting example embodiment) in the longitudinal direction of the tabletop. The distance is not limited to the length of the traverse device (the rack 108, in the illustrated non-limiting example embodiment). Thus, there is provided a compact mechanism for disposing a tabletop over a broader range of positions relative to the column, which increases the versatility of the surgical table.

Moreover, in embodiments of the invention (such as the illustrated embodiment) in which the surgical table includes a mechanism for inclining the tabletop relative to the horizontal about a transverse axis of the tabletop, due to the provision of the tabletop traverse drive mechanism there is provided a compact mechanism for inclining the tabletop at a steep angle relative to the horizontal when the tabletop is positioned at or near to one or other of its longitudinal limits relative to the column. Accordingly, there is provided a compact mechanism for disposing a tabletop in a still greater variety of different configurations, in order to increase the versatility of the surgical table.

In the illustrated embodiment, the driver of the tabletop traverse drive mechanism 100 comprises a single motor connected to both the first and second pinion gears 104, 106 for driving both the first and second pinion gears 104, 106. The use of a single motor minimises complexity of the tabletop traverse drive mechanism and complexity of control of the tabletop traverse drive mechanism. In variations to this embodiment, the driver may instead comprise a first motor connected to the first pinion gear 104 for driving the first pinion gear 104, and a second motor connected to the second pinion gear 106 for driving the second pinion gear 106.

In the illustrated embodiment, the first and second drive elements are able to mesh with the traverse device. Such meshing reduces or eliminates slipping between the drive elements and the traverse device, which results in smooth and steady traversing of the tabletop, reduced wear of the tabletop traverse drive mechanism, and the ability to accurately position the tabletop relative to the column. Each of the first and second drive elements is made from hardened steel and, preferably, has surfaces having a low coefficient of friction. In a variation to this embodiment, the first and second drive elements do not mesh with the traverse device. For example, the first and second drive elements may comprise first and second wheels with smooth circumferential surfaces, and the traverse device may comprise a smooth plate along which the first and second wheels are driven. In such embodiments, preferably one or both of the surface of the plate and the circumferential surfaces of the first and second wheels have a high coefficient of friction (e.g. through being made of rubber or an elastomer), to reduce or eliminate slipping between the wheels and the plate.

As discussed above, the tabletop 10 is traversable in a longitudinal direction relative to the column 8. The table 2 of the illustrated embodiment includes an assistance mechanism for helping medical staff using the table 2 to move the tabletop 10 relative to the column 8 in a selected longitudinal direction of the tabletop 10 to dispose the tabletop 10 and the column 8 at a predetermined relative position, such as a predetermined default or home position.

In dependence on movement instruction(s) received at the controller from the user interface of the surgical table 2, the controller is configured to control the tabletop traverse drive mechanism 100 to cause movement of the tabletop 10 relative to the column 8 between the first and second positions via the predetermined traverse position. When the tabletop 10 is at the predetermined traverse position relative to the column 8, the controller controls the tabletop traverse drive mechanism 100 to cause the movement of the tabletop 10 relative to the column 8 to be paused for a predetermined period of time. In this embodiment, the predetermined period of time is 2 seconds. However, in variations to this embodiment, the predetermined period of time may be any time between 0.05 and 5 seconds, more preferably between 0.1 and 3 seconds, more preferably between 0.25 and 2 seconds, and most preferably between 1 and 2 seconds. The controller is configured such that, if after elapse of the predetermined period of time the controller still is receiving from the user interface the movement instruction(s) to control the tabletop traverse drive mechanism 100 to cause the movement of the tabletop 10 relative to the column 8, then the controller controls the tabletop traverse drive mechanism 100 to cause the movement of the tabletop 10 relative to the column 8 to be resumed. The controller also is configured such that, if after elapse of the predetermined period of time the controller no longer is receiving from the user interface the movement instruction(s) to control the tabletop traverse drive mechanism 100 to cause the movement of the tabletop 10 relative to the column 8, then the controller controls the tabletop traverse drive mechanism 100 to cause the movement of the tabletop 10 relative to the column 8 not to be resumed.

In this embodiment, the table includes a sensor (not shown) communicatively connected to the controller. The sensor comprises a rotary encoder (not shown) fitted to the spindle of the motor and configured to output to the controller an indication of the current position of the spindle. Using the output of the rotary encoder, the controller keeps track of the current position of the spindle and, thus, is able to determine a current position of the tabletop 10 relative to the column 8. The controller determines when the tabletop 10 is at the predetermined traverse position relative to the column 8 using the output of the rotary sensor. The controller may determine when the tabletop 10 is at the predetermined traverse position relative to the column 8 based on the number of detected rotations of the motor of the tabletop traverse drive mechanism 100 since the tabletop 10 began moving from one or other of the first and second traverse positions.

The sensor may also or alternatively comprise a rotary potentiometer connected by a drive wheel to one of the drive elements 104, 106 and configured to output to the controller an indication of the current position of the drive element 104, 106. Using the output of the rotary potentiometer, the controller keeps track of the current position of the drive element 104, 106 and, thus, is able to determine a current position of the tabletop 10 relative to the column 8. Additionally or alternatively, a cable potentiometer may be used.

In variations to this embodiment, the sensor may comprise a micro switch mounted at the top of the column 8, and a portion of the tabletop 10 may be configured to actuate the micro switch when the portion of the tabletop 10 passes the micro switch. The micro switch and the portion of the tabletop 10 are relatively disposed so that the portion of the tabletop 10 actuates the micro switch when the tabletop 10 is at the predetermined traverse position relative to the column 8. In still further variations, the sensor could take forms other than a micro switch and/or could comprise components located at different places on the table.

In variations to this embodiment, the controller may determine when the tabletop 10 is at the predetermined traverse position relative to the column 8 based on time elapsed since the tabletop 10 began moving from one or other of the first and second traverse positions at a known speed. Other mechanisms for determining when the tabletop 10 is at the predetermined traverse position relative to the column 8 also are usable.

It will thus be appreciated that, through the provision of the assistance mechanism, users of the surgical table are alerted as to when the tabletop is at the predetermined traverse position relative to the column, and are given the predetermined period of time in which to cause the user interface to stop sending the movement instruction(s) to the controller. Thus, there is provided a mechanism for helping users of the surgical table to dispose the tabletop of the surgical table at the predetermined traverse position relative to the column.

The controller may be connected to memory storing instructions for causing the controller to carry out one of the inventive methods of the present invention. Such memory may be considered to be an example of a computer program product for causing an apparatus, such as the controller, to perform one of the inventive methods of the present invention.

Various modifications can be made to the above-described embodiments without departing from the scope of the present invention, which is defined by the claims.

For example, in variations to the illustrated embodiment, in addition to or instead of the surgical table being provided with the tabletop traverse drive mechanism for causing movement of the tabletop relative to the column in a selected longitudinal direction of the tabletop, the surgical table is provided with a tabletop traverse drive mechanism mounted between the underside of the tabletop and the top of the column for causing movement of the tabletop relative to the column in a selected transverse direction of the tabletop. Such an additional or alternative, respectively, tabletop traverse drive mechanism may have any or all of the features and operation of the illustrated tabletop traverse drive mechanism, but in order to permit movement of the tabletop relative to the column in a selected transverse direction of the tabletop rather than in a selected longitudinal direction of the tabletop. Through the provision of such an additional or alternative, respectively, tabletop traverse drive mechanism, the tabletop is movable relative to the column in the transverse direction of the tabletop over a distance that is greater than the length of the traverse device (which may be a rack, similar to the rack 108) in the transverse direction of the tabletop. The distance is not limited to the length of the traverse device. Thus, there is provided a compact mechanism for transversely positioning the tabletop e.g. within an imaging device in order to image a patient on the tabletop.

Moreover, in such variations to the illustrated embodiment, the surgical table may include an assistance mechanism for helping medical staff using the table to move the tabletop relative to the column in a selected transverse direction of the tabletop to dispose the tabletop and the column at a predetermined relative position, such as a predetermined default or home position.

In variations to the above-described embodiments, the surgical table may have none, or only either one, of the above-described assistance mechanisms.

The invention claimed is:

1. A surgical table comprising: a base for standing on a floor; a column extending from the base; a tabletop providing a patient support surface; and a tabletop traverse drive mechanism coupling the tabletop to the column, which tabletop traverse drive mechanism is for causing movement of the tabletop relative to the column in a selected longitudinal or transverse direction of the tabletop; wherein the tabletop traverse drive mechanism comprises a driver, first and second drive elements that are drivable by the driver, and a traverse device that is drivable by each of the first and second drive elements, the first and second drive elements being movably mounted on one of the column and the tabletop and the traverse device being mounted on the other of the column and the tabletop; and wherein the driver is operable to drive the first and second drive elements to drive the traverse device to cause movement of the tabletop relative to the column between a predetermined traverse position, at which both of the first and second drive elements are engaged with the traverse device, and a first traverse position, at which the first drive element is engaged with the traverse device and the second drive element is disengaged from the traverse device, wherein the first and second drive elements are first and second pinion gears, wherein the traverse device is a rack.

2. A surgical table according to claim 1, wherein the driver is operable to drive the first and second drive elements to drive the traverse device to cause movement of the tabletop relative to the column to a second traverse position, at which the second drive element is engaged with the traverse device and the first drive element is disengaged from the traverse device.

3. A surgical table according to claim 1, wherein the tabletop traverse drive mechanism is for causing movement of the tabletop relative to the column in a selected longitudinal direction of the tabletop.

4. A surgical table according to claim 1, wherein the first and second drive elements are movably mounted on the column and the traverse device is mounted on the tabletop.

5. A surgical table according to claim 1, wherein the first and second drive elements are rotatably mounted on the one of the column and the tabletop.

6. A surgical table according to claim 5, wherein the first and second drive elements are mounted for rotation about respective first and second axes that are both perpendicular to the longitudinal direction of the tabletop, or that are both parallel to the longitudinal direction of the tabletop.

7. A surgical table according to claim 6, wherein one or each of the first and second axes is perpendicular to a lateral direction of the tabletop, which lateral direction of the tabletop is perpendicular to the longitudinal direction of the tabletop.

8. A surgical table according to claim 6, wherein one or each of the first and second axes is parallel to a lateral direction of the tabletop, which lateral direction of the tabletop is perpendicular to the longitudinal direction of the tabletop.

9. A surgical table according to claim 1, wherein the first and second drive elements are meshed with the traverse device when the tabletop is at the predetermined traverse position.

10. A surgical table according to claim 1, wherein the traverse device is linear and aligned with the longitudinal direction of the tabletop.

11. A surgical table according to claim 1, wherein the first and second drive elements are spaced apart in a direction that is parallel to the longitudinal direction of the tabletop.

12. A surgical table according to claim 1, wherein the driver comprises a motor connected to both the first and second drive elements for driving both the first and second drive elements.

13. A surgical table according to claim 2, comprising a controller for controlling operation of the tabletop traverse drive mechanism, wherein the controller is configured to control the tabletop traverse drive mechanism to cause movement of the tabletop relative to the column between the first and second traverse positions via the predetermined traverse position, and configured, when the tabletop is at the predetermined traverse position relative to the column, to control the tabletop traverse drive mechanism to cause the movement of the tabletop relative to the column to be paused for a predetermined period of time.

14. A surgical table according to claim 13, comprising a sensor for sensing, and for notifying the controller of, a relative position of the tabletop and the column.

15. A surgical table according to claim 14, wherein the sensor is for sensing, and for notifying the controller of, when the tabletop is at the predetermined traverse position relative to the column.

16. A surgical table according to claims 13, wherein the predetermined period of time is between 0.05 and 5 seconds.

17. A surgical table according to claim 16, wherein the predetermined period of time is between 0.1 and3 seconds.

18. A surgical table according to claim 17, wherein the predetermined period of time is between 0.25 and 2 seconds.

* * * * *

UNITED STATES PATENT AND TRADEMARK OFFICE
CERTIFICATE OF CORRECTION

PATENT NO. : 10,149,794 B2
APPLICATION NO. : 14/896938
DATED : December 11, 2018
INVENTOR(S) : Matt Clayton and Mick Gray Page 1 of 1

It is certified that error appears in the above-identified patent and that said Letters Patent is hereby corrected as shown below:

On the Title Page

• PCT Filing Date amend "June 14, 2014" to -- June 13, 2014 --.

Signed and Sealed this
Fifth Day of February, 2019

Andrei Iancu
*Director of the United States Patent and Trademark Office*